United States Patent [19]

Stahura

[11] Patent Number: 4,611,498

[45] Date of Patent: Sep. 16, 1986

[54] COLLECTION RECEPTACLE AND METHOD

[75] Inventor: Richard P. Stahura, Indiana, Pa.

[73] Assignee: Martin Engineering Company, Neponsit, Ill.

[21] Appl. No.: 789,375

[22] Filed: Oct. 21, 1985

[51] Int. Cl.⁴ .................. G01N 1/08; G01G 19/00
[52] U.S. Cl. .................... 73/864.41; 73/863.91; 73/864.51; 177/50
[58] Field of Search ........... 73/864.41, 864.51, 863.91, 73/432 GM, 432 R; 177/50; 206/305, 205; 220/90; 198/499, 498, 497; 15/256.5

[56] References Cited

U.S. PATENT DOCUMENTS

| 1,848,450 | 3/1932 | Williamson | 220/90 X |
| 2,759,606 | 8/1956 | Nippert | 198/497 X |
| 4,189,046 | 2/1980 | Ward | 198/499 |
| 4,347,749 | 4/1982 | Heintze | 73/864.51 X |
| 4,398,412 | 8/1983 | Huneidi | 73/864.41 X |
| 4,489,823 | 12/1984 | Gordon | 198/499 |

FOREIGN PATENT DOCUMENTS 832393  5/1981  U.S.S.R. ..................... 73/864.41

Primary Examiner—Stewart J. Levy
Assistant Examiner—Tom Noland
Attorney, Agent, or Firm—Mann, McWilliams, Zummer & Sweeney

[57] ABSTRACT

A collection receptacle and method of using same to scrape and collect residue from a moving surface, such as a conveyor belt, for a predetermined time period in order to analyze and evaluate both the nature and amount of residue carried by the moving surface. Information derived from the collection procedure is of assistance in determining the type and extent of conveyor belt cleaning equipment required. The receptacle consists of a container with an open upper end and one or more scraper blades extending upwardly above the side walls of the container. A pair of spacer arms also extend upwardly from the container and engage the moving surface.

6 Claims, 5 Drawing Figures

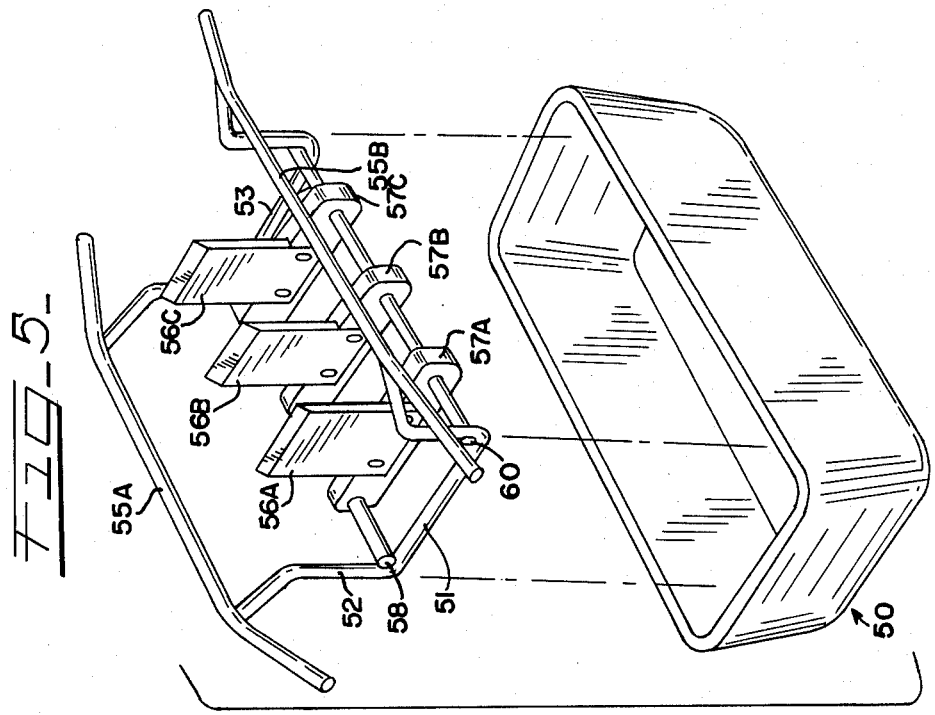
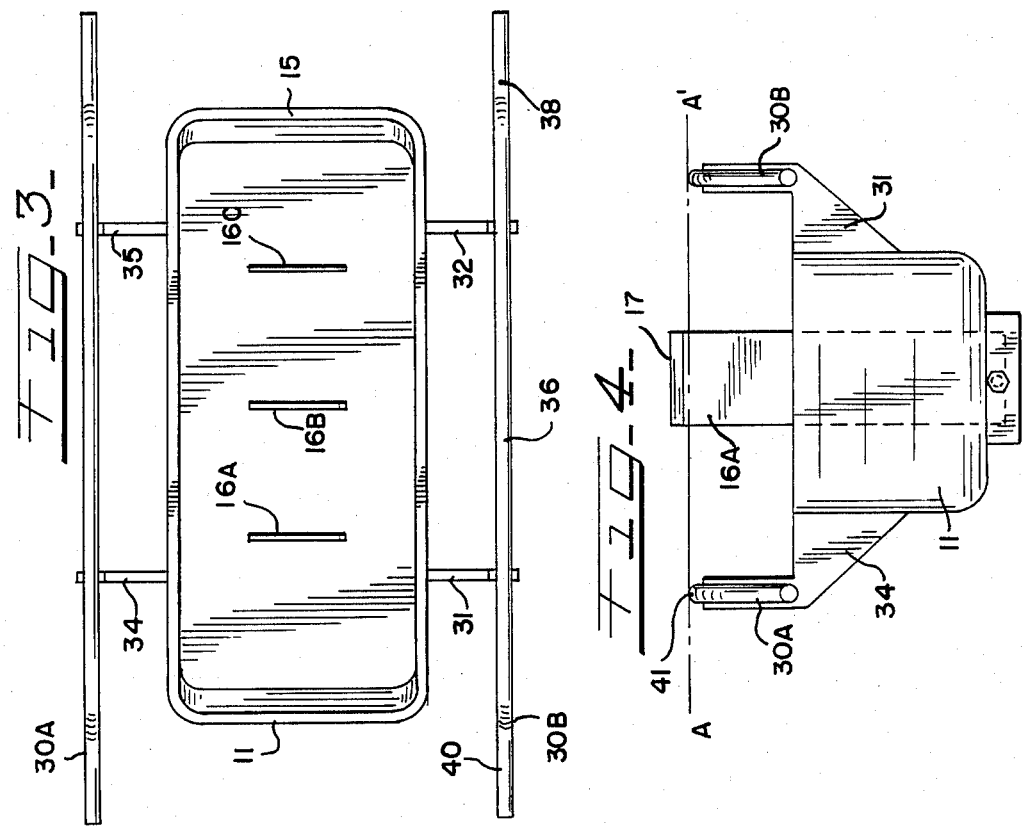

COLLECTION RECEPTACLE AND METHOD

BACKGROUND OF THE INVENTION

It has been known in the art to provide various types of conveyor belt cleaners including blade-type cleaners in which a scraper blade engages a moving conveyor belt to remove materials which are sometimes deposited in a hopper. Typical of prior art arrangements are those shown in U.S. Pat. Nos. 999,515, 1,975,591, 2,885,069, 3,414,116, and 3,474,893. None of these references, however, utilizes a removable collection receptacle which can be placed into engagement with a moving surface to scrape residue from the surface for a predetermined time and collect the residue in the container for later measurement and analysis.

SUMMARY OF THE INVENTION

The present invention provides both an apparatus for and a method of collecting and measuring the amount of residue carried by a segment of a moving surface during a predetermined time period. The device consists of a collection receptacle with scraper blades extending from and above the container sides so as to engage the moving surface. The receptacle also includes a pair of spacer arms disposed on opposite sides of the receptacle positioned at a height lower than the scraping edge of the blades and higher than the top of the container side wall. The spacer arms provide a reference surface when urged into engagement with the moving surface. A method is described for using this apparatus to collect residue removed from a moving surface during a given period of time. The container can thus be used as a gauge to compare the residue removed from one belt compared to another operating under the same or different conditions.

DESCRIPTION OF THE DRAWINGS

FIG. 3 is a top view of the receptacle shown in FIG. 1.

FIG. 4 is an end view of the receptacle of FIG. 3.

FIG. 5 is an exploded perspective view of a modified embodiment of the collection receptacle of the present invention.

DESCRIPTION OF THE PREFERRED EMBODIMENT

Figure 1:
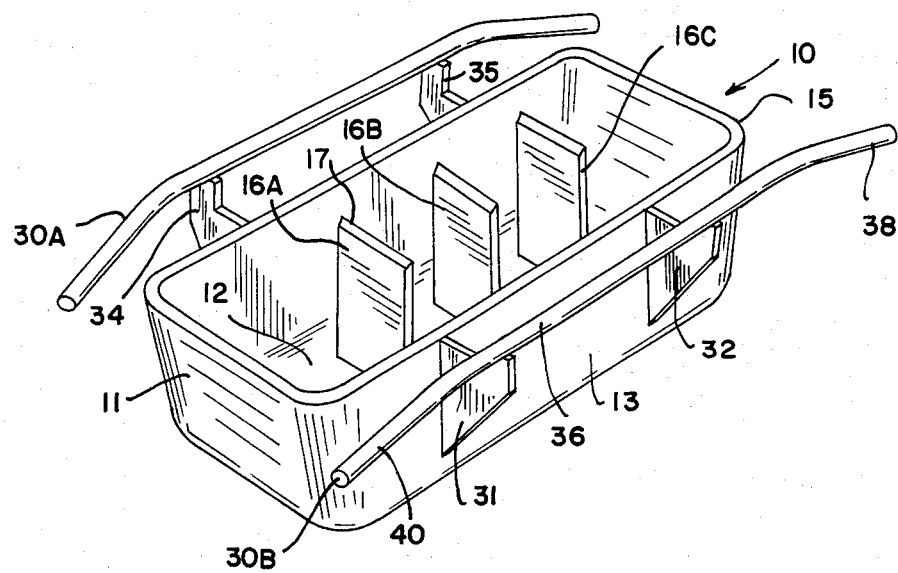
FIG. 1 is a top perspective view showing the collection receptacle of the present invention.

As best shown in FIG. 1, a collection receptacle 10 is provided for engaging a moving surface and removing and collecting residue from same. The receptacle includes a container 11 with a bottom surface 12 enclosed by a side wall 13 extending about its entire periphery. The side wall 13 includes an upper edge 15 which is of uniform height around the periphery of the container. The container has been illustrated as generally rectangular in configuration with rounded corners, but any suitable shape can be utilized. The container is open at its upper end so as to receive and collect material from above. The container is generally formed of metal, but where desired, may also be formed of rigid, transparent plastic to enable viewing of the contents.

Extending upwardly from the bottom of the container are three scraper blades 16A, 16B, and 16C. It is possible to utilize a single scraping blade, two blades, or more than three blades, depending upon the application, but three blades has been determined to represent the preferred embodiment. Each of these blades is formed of a resilient material, preferably spring steel, in order to enable flexing of the blades about their vertical axis. The blades 16 define a sharpened scraping edge 17 at their upper end. One embodiment which has performed well, for test purposes, consists of a metal container 6 ¾ inches in length from outside wall to outside wall, 4 3/16 inches wide, and approximately 1 ⅞ inches deep.

Figure 2:
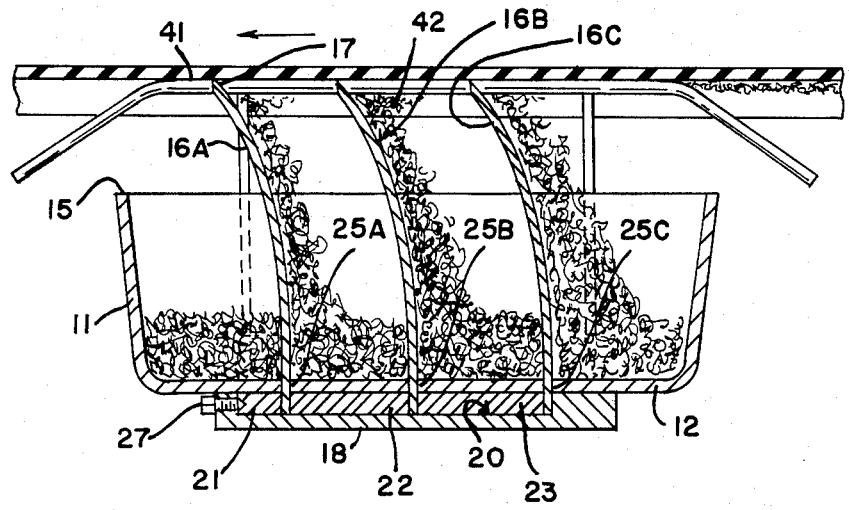
FIG. 2 is a side view showing the collection receptacle operatively engaged with a moving conveyor belt.

As best shown in FIG. 2, a base member 18 is disposed below the bottom surface 12 of the container 11. Slidably received within a chamber 20 formed in the base member 19 are a plurality of inserts 21, 22, 23, the purpose for which will become apparent. A plurality of slots 25A, 25B, and 25C are located in the bottom surface 12 of the container extending approximately the width of the scraper blades 16. As illustrated in FIG. 2, the blades 16 extend through the slots 25 into the chamber 20. Inserts 21, 22, and 23 abut the blades 16A, 16B, and 16C on adjacent sides. Securing means, in the form of a set screw 27, is provided in the base member 18 adjacent one end of the insert 21. When the blades 16 are in place extending into the chamber 20 through the slots 25, the set screw 27 is tightened, thereby securing the blades in place. When removal or replacement of the blades is desired, the set screw 27 is loosened and the blades are removed from the container. As shown in FIG. 4, the blades 16 extend above the upper edge 15 of the container.

A pair of spacer arms 30A and 30B are shown disposed on either side of the container. Brackets 31 and 32 are connected to the side wall of the container and support spacer arm 30B. Brackets 34, 35 are connected to the other side of the container 11 and support the spacer arm 30A. The arms 30A and 30B include a horizontally-extending central section 36 and a pair of downwardly inclined end portions 38 and 40. The dotted line A, A', shown in FIG. 4, lies along a plane parallel to an upper edge 41 of the central section 36 of spacer arms 30A and 30B which defines an engaging surface. As best seen in FIG. 4, the scraping edge 17 of arms 16 extends above the engaging surface of the spacer arms 30A, 30B when the container is not in an operational mode. The recommended height of blade 16 above surface 41 is between ⅛ inch and ⅜ inch, which may be adjustable.

FIG. 2 shows the collection receptacle of the present invention in operation. In order to determine the composition and extent of the residue carried by a moving surface, such as a conveyor belt, it is desirable to obtain a representative sample of such residue. For comparison and evaluation purposes, one will need to know how much residue will be removed from a designated portion of a conveyor belt during a predetermined period of time. First the container 11, shown in FIG. 1, is weighed empty. The container is then urged into engagement with the moving surface for a predetermined period of time as, for example, ten seconds, during which time the scraper blades 16 clean a portion of the belt and remove residue traveling on the undersurface of the belt. This is accomplished by exerting pressure against the underside of the container, moving it upwardly until the cleaning edges 17 of the blades 16 contact the undersurface of the moving belt. The container is urged to move upwardly an additional distance until the upper or engagement surface 41 of both spacer arms 30A and 30B is in contact with the lower surface of the conveyor belt. Assuming the belt is moving in the direction of the arrow in FIG. 2, the blades 16 will flex counterclockwise about their vertical axis so that the cleaning edges 17 are aligned at the same height as the upper surface 41 of the spacer arms. Each time the collection receptacle is used, the spacer arms will insure that the blades 16 contact the moving surface with the same degree of force and at the same angle. If the conveyor belt traveling in the direction opposite the arrow shown in FIG. 2, the container will be rotated 180° from the position shown in FIG. 2 so that the cleaning edge 17 of the blades 16 will be properly oriented to the direction of conveyor belt travel.

As shown in FIG. 2, with the blades 16 contacting a portion of the moving belt surface, the blades scrape from the surface the residue which is carried on the undersurface of the belt. This residue, illustrated as 42 in FIG. 2, falls along the walls of the scraper blades and is collected in the container 11. Whatever residue is not removed by blade 16C can be scraped from the surface by blades 16B or 16A. After the passage of a predetermined period of time, the container is removed from the belt and weighed again. The difference between the weight of the container plus contents minus the weight of the container empty is the amount of residue material removed from a portion of the moving surface during the designated time. This information can be evaluated, taking into account the density of the particular residue being carried on the belt, the moisture content, the belt speed, and other critical factors. Such a procedure will enable an engineer or sales person to evaluate the degree of contamination of a belt operating in a particular environment carrying a particular material and will enable such person to recommend the proper type of equipment for cleaning that particular belt operating under the given conditions. Thus, in effect, the receptacle and its method of use function as a gauge to compare the contamination of belts operating in different environments. Utilizing this aparatus and method will also enable belt operators to utilize the collection receptacle and method downstream of an existing conveyor belt cleaning arrangement in order to test the effectiveness of the belt cleaner and, in some instances, to compare the effectiveness of different types of cleaners installed along different segments of a belt.

The collection receptacle 50 shown in FIG. 5 is a modified embodiment of the present invention which is especially adapted for collecting specimens from moving surfaces in the field. It features a readily removable spacer bar and blade assembly 51 consisting of supporting frame members 52 and 53 connected to spacer arms 55A and 55B. Scraper blades 56A, 56B, and 56C are fastened to support members 57A, 57B, and 57C, respectively. The support members 57 are, in turn, carried by rods 58 and 60, which, in turn, rest upon and are supported by frame members 52 and 53.

The embodiment of FIG. 5 is particularly adapted for use in the field when a large number of samples from different belts or different segments of a given belt are required. The person responsible for accumulating the samples will initially weigh and mark all of the empty receptacles. The snap-in spacer and blade assembly 51 is then inserted into a given container 50. That container is engaged against the moving surface carrying the residue in exactly the same manner as described for the embodiment of FIG. 2. After the predetermined accumulation period has elapsed, the receptacle and contents are removed from the moving surface and the spacer and blade assembly 51 is removed from the container. The person collecting samples must be sure that all residue clinging to the removable assembly 51 is brushed or tapped from the assembly into the container. The container 50 can then be sealed and appropriately marked for evaluation at a later time. The snap-out assembly can then be placed in another container for collection of a second sample. This procedure can be repeated any number of times until the requisite number of samples have been collected and sealed. The containers can then be taken back to a laboratory or other site for weighing and further evaluation.

Various features of the invention have been particularly shown and described in connection with the illustrated embodiments of the invention, however, it must be understood that these particular arrangements merely illustrate and that the invention is to be given its fullest interpretation within the terms of the appended claims.

What is claimed is:

1. A receptacle for collecting and weighing the residue carried by a moving surface including a partially enclosed container, open at its upper end, defining a bottom surface and a side wall with an upper edge, one or more resilient blades extending upwardly from said bottom surface, each of said blades including a scraping edge at the upper end thereof and each blade extending to a height above said upper edge of said side wall when blade is in its unflexed state, and spacer means associated with and extending upwardly from said container, said spacer means defining an engaging surface positioned such that said engaging surface is above said upper edge of said container side wall but is below said scraping edge of said blade when said blade is in its unflexed, vertical position, whereby when said receptacle is urged toward a moving surface with sufficient force, said engaging surface of said spacer means will contact said moving surface, said resilient blade will flex until said scraping edge of said blade is at the same height as said engaging surface of said spacer means and said blade will scrape residue from said moving surface into said container.

2. A collection receptacle as in claim 1 in which said resilient blades are removable from said container.

3. A collection receptacle as in claim 1 in which said spacer arms and said blades are removable from said container.

4. A collection receptacle as in claim 1 in which said spacer means includes a pair of spacer arms, each disposed on opposite sides of said container at the same height, each arm definig one said engaging surface.

5. A collection receptacle as in claim 1 in which said spacer means and said blades are connected together as a unit which is readily removable from said container.

6. A method of collecting and measuring the residue carried by a moving surface utilizing a receptacle which includes one or more upstanding, resilient scraper blades and a spacer means for positioning said receptacle with respect to said moving surface, the steps of the method comprising weighing said empty receptacle, placing said scraper blades into contact with said moving surface with sufficient force to cause flexing of the blades until the spacer means contacts the moving surface, maintaining said scraper blades and said spacer means in contact with said moving surface for a predetermined period of time while said blades remove residue from said moving surface which residue is deposited in said receptacle, and removing said receptacle from said moving surface and weighing said receptacle and its residue content.

* * * * *